US010729779B2

(12) United States Patent
Kageshima et al.

(10) Patent No.: US 10,729,779 B2
(45) Date of Patent: Aug. 4, 2020

(54) COMPOSITION HAVING ANTIFUNGAL ACTIVITY

(71) Applicants: WAKO FILTER TECHNOLOGY Co., LTD., Tokyo (JP); TEIKYO UNIVERSITY, Tokyo (JP)

(72) Inventors: Hiroki Kageshima, Nagareyama (JP); Akira Saito, Toride (JP); Yoichi Murakami, Koga (JP); Shigeru Abe, Hachioji (JP); Kazumi Hayama, Hachioji (JP); Miki Takahashi, Hachioji (JP); Miho Abe, Hachioji (JP)

(73) Assignees: Wako Filter Technology Co., Ltd., Tokyo (JP); Teikyo University, Tokyo (JP)

( * ) Notice: Subject to any disclaimer, the term of this patent is extended or adjusted under 35 U.S.C. 154(b) by 10 days.

(21) Appl. No.: 15/755,717

(22) PCT Filed: Aug. 31, 2016

(86) PCT No.: PCT/JP2016/075499
§ 371 (c)(1),
(2) Date: Feb. 27, 2018

(87) PCT Pub. No.: WO2017/038872
PCT Pub. Date: Mar. 9, 2017

(65) Prior Publication Data
US 2019/0022238 A1 Jan. 24, 2019

(30) Foreign Application Priority Data

Aug. 31, 2015 (JP) ................................. 2015-171397

(51) Int. Cl.
| | | |
|---|---|---|
| *A61K 47/64* | (2017.01) | |
| *A61K 31/045* | (2006.01) | |
| *A61K 31/722* | (2006.01) | |
| *A61K 31/19* | (2006.01) | |
| *A61K 31/122* | (2006.01) | |
| *A61K 31/10* | (2006.01) | |
| *A61K 47/61* | (2017.01) | |
| *A61P 31/10* | (2006.01) | |
| *A61K 31/20* | (2006.01) | |
| *A61K 38/47* | (2006.01) | |

(52) U.S. Cl.
CPC ............ *A61K 47/64* (2017.08); *A61K 31/045* (2013.01); *A61K 31/10* (2013.01); *A61K 31/122* (2013.01); *A61K 31/19* (2013.01); *A61K 31/20* (2013.01); *A61K 31/722* (2013.01); *A61K 38/47* (2013.01); *A61K 47/61* (2017.08); *A61P 31/10* (2018.01); *C12Y 302/01017* (2013.01)

(58) Field of Classification Search
None
See application file for complete search history.

(56) References Cited

FOREIGN PATENT DOCUMENTS

| | | |
|---|---|---|
| JP | 2003089652 A | 3/2003 |
| JP | 2003089653 A | 3/2003 |
| JP | 2005187401 A | 7/2005 |
| JP | 2013040156 A | 2/2013 |

OTHER PUBLICATIONS

Duan, J. et al., J. Food Sci. 2007, vol. 72, pp. M355-M362.*
WAFTEC 2015 promotional material downloaded from w3.waftec.jp/img/bioguide.pdf.*
Wang, L-d. et al., J. East. China Univ. Sci. Tech, 2013, vol. 39, pp. 284-288.*
Pohl, C. et al., chapter in "Science against microbial pathogens," A. Menez-Vilas, ed., pub. by Informatex 2011, pp. 61-71.*
Leite, M. et al., Med. Mycol. 2015 vol. 53, pp. 275-284.*
Gupta, et al., "Protein Phylogenies and Signature Sequences: A Reappraisal of Evolutionary Relationships among Archaebacteria, Eubacteria, and Eukaryotes", Microbiol. Mol. Biol. Rev., vol. 62, No. 4, pp. 1435-1491, 1998.
Ghannoum, et al., "Antifungal Agents: Mode of Action, Mechanisms of Resistance, and Correlation of These Mechanisms with Bacterial Resistance", Clinical Microbiology Reviews, vol. 12, No. 4, pp. 501-517, Oct. 1999.
Gold, et al., "Amphotericins A and B, antifungal antibiotics produced by a streptomycete. I. In vitro studies", Antibiotics Annual, 3, pp. 579-586, Jan. 1, 1955.
Wang et al., "Bactericidal Properties of Chitosan and Lysozyme Composite System," Journal of East China University of Science and Technology (Natural Science Edition) vol. 39, No. 3, 2013, pp. 284-291.
Bergsson et al., "In Vitro Killing of Candida albicans by Fatty Acids and Monoglycerides," Antimicrobial Agents and Chemotherapy, Nov. 2001, vol. 45, No. 11, p. 3209-3212.
Song et al., "Emulsifying properties and bactericidal action of chitosan-lysozyme conjugates," Food Research International, 2002, vol. 35, pp. 459-466.

(Continued)

*Primary Examiner* — Heidi Reese
(74) *Attorney, Agent, or Firm* — BakerHostetler

(57) ABSTRACT

The present invention provides a composition having an antifungal activity without depending on conventional compositions having anticandidal activity or combinations of such compositions. The composition comprises a complex of lysozyme bonded to chitosan. The composition according to the present invention is applicable to candidiasis of the skin and mucous membranes, in particular, oral candidiasis and vagina candidiasis affecting a large number of patients and can ameliorate the symptoms of these diseases, heal the same and prevent infection of the same. The composition comprises a complex of lysozyme, which has been widely used as a highly safe natural food additive, with a polysaccharide and, therefore, can reassure patients who use the same and ease their burden. The composition according to the present invention comprises a complex of lysozyme, which is a highly safe natural food additive, with a polysaccharide and, therefore, can be safely used by patients without considering any risk.

1 Claim, 16 Drawing Sheets

(56) References Cited

OTHER PUBLICATIONS

Ninomiya et al., "Effects of Inhibitory Activity on Mycelial Growth of Candida albicans and Therapy for Murine Oral Candidiasis by the Combined Use of Terpinen-r-ol and a Middle-chain Fatty Acid, Capric Acid," Journal of the Pharmaceutical Society of Japan, Jan. 2013, vol. 133, No. 1, pp. 133-140.

WAFTEC Bio & Healthcare Jigyo Suishin Honbu no Shokia Shiryo, [online], Aug. 28, 2015, [retrieval date Sep. 29, 2016], Internet:<URL:http://www.waftec.jp/mg/bio_guide/pdf>.

* cited by examiner

COMPOSITION HAVING ANTIFUNGAL ACTIVITY

REFERENCE TO RELATED APPLICATIONS

This application is the U.S. national stage of International Application No. PCT/JP2016/075499, filed Aug. 31, 2016, which claims the priority from Japan Patent Application No. 2015-171397, filed Aug. 31, 2015, the entire contents of which are incorporated herein by reference.

TECHNICAL FIELD

This invention relates to a novel composition having an antifungal activity.

TECHNICAL BACKGROUND

One of the problems that may arise during the treatment of HIV and cancer as well as during organ transplants is the risk of infection caused by microorganisms. The development of antibiotics that fight bacterial infections is already well established. The appearance of drug-resistant bacteria such as MRSA and VRE is already causing problems, however, more serious than these are infections caused by fungi. In particular, candidiasis caused by *Candida albicans* and aspergillosis caused by genus *Aspergillus* are large obstacles during transplant operations.

Yeasts and filamentous fungi are eukaryotes, and are referred to as fungi in comparison to bacteria, which are prokaryotes. Certain types of fungi exhibit pathogenicity towards humans and animals, and are regarded as causative microorganisms of fungal infections. The pathogenicity of these fungi is generally weak, however, they sometimes cause severe symptoms in patients who already have lowered resistance.

Because the various illnesses generated by fungi have an enormous effect on the health of humans and animals, the development of new medicines that are useful in the treatment thereof is greatly desired. Moreover, the intrusion of filamentous fungi in houses as a result of condensation and the like, which is reflective of modern housing conditions, causes symptoms such as allergies and the like in humans, and has a deleterious effect on the health of humans and animals. The development of new antifungal agents is desired as an effective countermeasure against such phenomena.

Here, preparations that inhibit *Candida* mycelial growth are described in Patent document 1 and Non-patent document 1.

In Patent document 1 it is disclosed that a synergistic effect in anticandidal activity against in vitro *Candida* mycelial growth is evident if capric acid (decanoic acid) is used in combination with any one of geraniol, eugenol, or citral. Moreover, it is also disclosed in Patent document 1 that, in oral candidiasis models in mice, a combination of capric acid and ginger essential oil had the greatest effect towards improving tongue symptoms.

Furthermore, it is disclosed in Non-patent document 1 that a synergistic effect in anticandidal activity against in vitro *Candida* mycelial growth is evident if capric acid is used in combination with terpinen-4-ol. Moreover, it is also disclosed in Non-patent document 1 that, in oral candidiasis models in mice, reliable therapeutic effects including a reduction in the viable bacteria count were apparent when capric acid and terpinen-4-ol were used in combination.

However, the aforementioned Patent document 1 and Non-patent document 1 disclose nothing more than the combined effect of using a medium chain fatty acid such as decanoic acid, which is known to have anticandidal activity, with a terpene alcohol such as terpinen-4-ol, which, in the same way, is also known to have anticandidal activity.

Furthermore, as is shown in Patent document 2, taking note of the fact that a complex of lysozyme and chitosan (30 kDa) has antibacterial properties, applications of this complex to foodstuffs and cosmetics may be considered. This complex is extremely safe, and imparts a stability to the lysozyme whose importance is emphasized by product design and the like, so as to further broaden the antibacterial spectrum.

However, nothing apart from the fact that this complex has antibacterial activity against *Escherichia Coli* K12 is disclosed, and any antibacterial activity against fungi such as genus *Candida* and genus *Aspergillus* has not been confirmed.

Documents of the Prior Art

Patent Documents

[Patent document 1] Japanese Unexamined Patent Application (JP-A) No. 2013-40156
[Patent document 2] Japanese Unexamined Patent Application (JP-A) No. 2005-187401

Non-Patent Documents

[Non-patent document 1] Kentaro NINOMIYA, et. al., "Effects of Inhibitory Activity on Mycelial Growth of *Candida albicans* and Therapy for Murine Oral Candidiasis by the Combined Use of Terpinen-4-ol and Middle-chain Fatty Acid, Capric Acid", Journal of the Pharmaceutical Society of Japan, The Pharmaceutical Society of Japan, Jan. 1, 2013, Vol. 133, Issue 1, pp. 133-140.

DISCLOSURE OF THE INVENTION

Problems to be Solved by the Invention

In contrast, the inventors of the present application performed strenuous investigations in order to provide a novel composition having an antifungal activity without having to rely on existing compositions having anticandidal activity or on combinations of such compositions. In the course of these investigations, the inventors of the present application discovered that a complex formed by bonding lysozyme to chitosan exhibited antifungal activity against fungi such as *Candida*.

Means for Solving the Problem

Namely, a composition having an antifungal activity according to the present invention is characterized in comprising a complex formed by bonding lysozyme to chitosan. A *Candida* proliferation suppressing action or a Malassezia fungi proliferation suppressing action are included in this antifungal activity. In other words, this composition contains a *Candida* proliferation suppressing composition, a *Malassezia* fungi proliferation suppressing composition, or a *Trichophyton* proliferation suppressing composition. Effects of this composition having an antifungal activity are described below.

It is desirable that a composition having an antifungal activity further comprises terpene alcohol or a fatty acid.

Examples of a terpene alcohol include geraniol, hinokitiol, menthol, and terpinen-4-ol.

It is desirable that the fatty acid is a fatty acid having a carbon number of 8 to 12. Specifically, fatty acids such as caprylic acid (carbon number 8), capric acid (carbon number 10), and lauric acid (carbon number 12) may be considered.

Effects of the Invention

According to the present invention, the effect of suppressing Candida infections in skin and mucous membranes is achieved. Accordingly, an effect of the present invention is that the present invention can be applied to candidiasis in skin or mucous membranes, and, in particular, to oral candidiasis and vaginal candidiasis which afflict a large number of patients, and can improve symptoms, cure diseases, and prevent infections that may arise therefrom. Moreover, Lysozyme is widely used as an extremely safe, natural food additive, and a composition having an antifungal activity that uses a complex of lysozyme and a polysaccharide is able to reassure a patient who uses it and alleviate their suffering.

Additionally, oral candidiasis and vaginal candidiasis tend to readily recur. However, there are limits to the application of antifungal agents due to side effects and the risk of resistant bacteria appearing. The present invention uses a complex of lysozyme, which is an extremely safe, natural food additive, and a polysaccharide, and can therefore be safely used by a patient without risks such as those described above needing to be considered.

Furthermore, by using this composition having antifungal activity as a Malassezia fungi proliferation suppressing composition, it is possible to prevent and ameliorate seborrheic dermatitis which occurs on the skin of humans and animals. Additionally, by using this composition having antifungal activity as a Trichophyton proliferation suppressing composition, it is possible to prevent and ameliorate Trichophyton infections such as athletes foot which occur on the skin of humans.

EMBODIMENTS FOR IMPLEMENTING THE INVENTION

Figure 1:
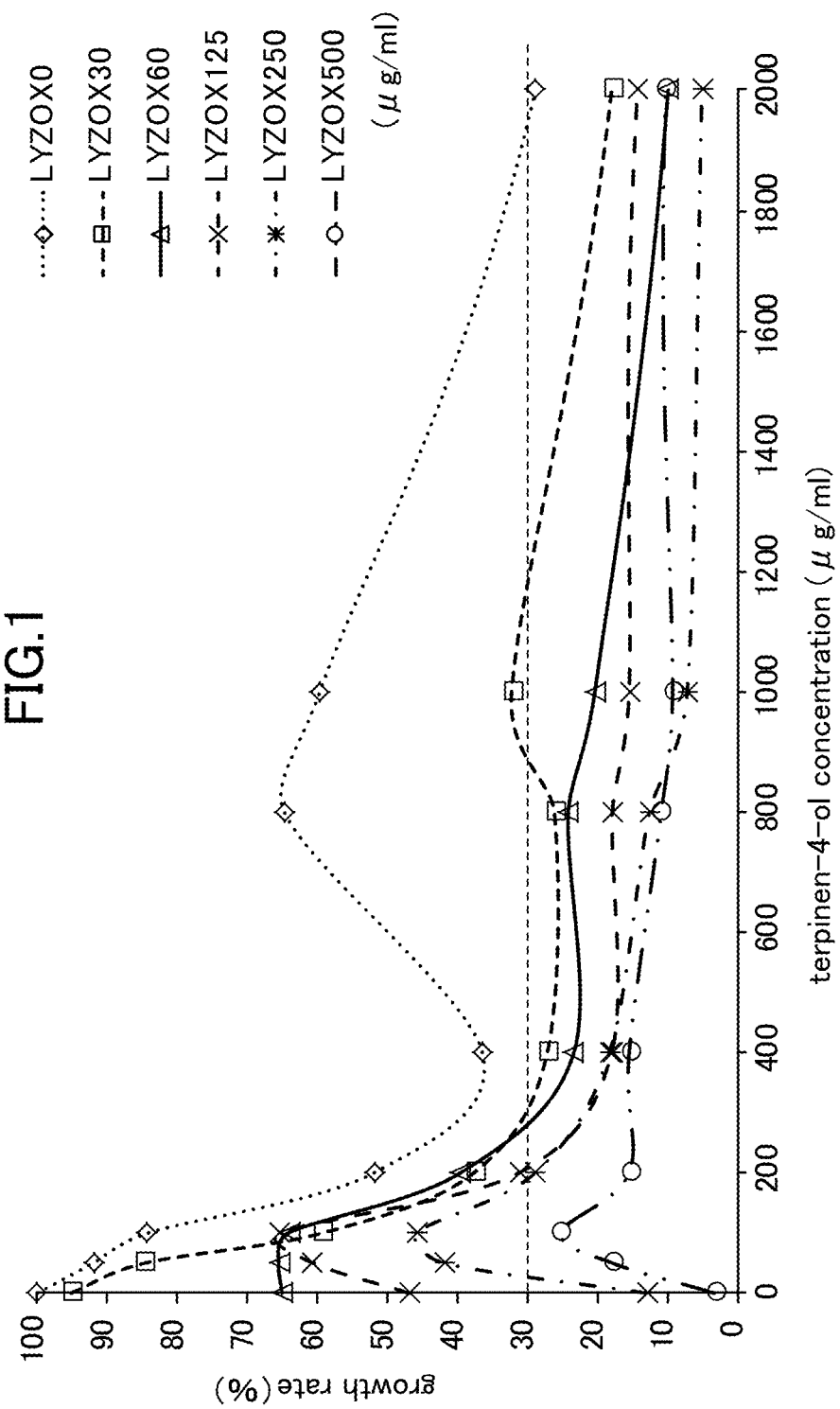
FIG. 1 is a view showing Candida growth rates when a lysozyme-chitosan complex is used in combination with terpinen-4-ol.

Hereinafter, the present invention will be described in detail.

1. First Embodiment

A composition having an antifungal activity according to a first embodiment contains a complex formed by bonding lysozyme to chitosan (in water-soluble form having a molecular weight of not more than 25000 Da). Note that, in the present embodiment, chitosan having a molecular weight of 14000 Da is used. Either chicken-derived lysozyme or human-derived lysozyme may be used.

The lysozyme-chitosan complex of the present invention can be manufactured by bonding lysozyme and chitosan together via a Maillard reaction. Because bonding the lysozyme and chitosan together via a Maillard reaction causes most of or all of the antigenic structure in the lysozyme to be masked, even if there is some absorption of the lysozyme-chitosan complex, it is still difficult for this to cause an allergy.

The specific manufacturing method is as follows.

Quantities of lysozyme and chitosan are dissolved in water such that the lysozyme/chitosan mass ratio is more preferably from 60/40 to 40/60, and the total content of lysozyme and chitosan in the aqueous solution is adjusted so as to be from 5 to 30% by mass. The resulting aqueous solution is then freeze-dried so as to be changed into powder form. This obtained powder is then made to undergo a Maillard reaction for a period of 2 to 20 days, and more preferably a period of 7 to 14 days in conditions of a temperature of 55 to 80° C., and more preferably a temperature of 55 to 65° C., and a relative humidity of 50 to 80%, and more preferably a relative humidity of 60 to 70%. By performing this process the lysozyme-chitosan complex of the present invention can be manufactured.

In the formation of the lysozyme-chitosan complex of the present invention, the formation of a polymer material in the form of a protein-chitosan complex can be confirmed using a plate obtained via SDS (sodium dodecyl sulfate-polyacrylamide) electrophoresis that has undergone dyeing processing.

The composition having an antifungal activity of the present invention will now be described.

In order to have a greater antibacterial activity, the composition having an antifungal activity of the present invention preferably contains 10 to 100% by mass of the lysozyme-chitosan complex, and more preferably 30 to 100% by mass thereof, and most preferably 50 to 100% by mass thereof.

Note that constituents such as dextrin and lecithin and the like can be used in addition to the lysozyme-chitosan complex in the composition having an antifungal activity. The content of these other constituents present in addition to the lysozyme-chitosan complex in the composition having an antifungal activity is preferably 0 to 90% by mass, more preferably 0 to 70% by mass, and most preferably 0 to 50% by mass.

2. Second Embodiment

A composition having an antifungal activity according to a second embodiment contains a complex formed by bonding lysozyme to chitosan via a Maillard reaction, together with a terpene alcohol. Note that examples of a terpene alcohol include geraniol, hinokitiol, menthol, and terpinen-4-ol, and the like. These terpene alcohols are plant essential oil components, and it is also possible to use plant essential oils that contain these terpene alcohols.

3. Third Embodiment

A composition having an antifungal activity according to a third embodiment contains a complex formed by bonding lysozyme to chitosan via a Maillard reaction, together with a fatty acid. Note that examples of a fatty acid include caprylic acid (carbon number 8), capric acid (carbon number 10), and lauric acid (carbon number 12).

EXAMPLES

The present invention will now be described in further detail with examples being provided, however, the present invention is not limited solely to these examples. Note that, in the following examples, a lysozyme-chitosan complex may also be referred to as LYZOX (Registered Trademark of Wako Filter Technology Co. Ltd.).

[Example 1] Inhibitory Activity of LYZOX, terpinen-4-ol, and Decanoic Acid Against *Candida* Mycelial Growth Methods of performing an in vitro inhibition test for yeast-form and mycelial growths of *Candida* are well-established, and as a result, the MIC (minimum inhibitory concentration) of various types of material can be measured.

A clinical isolate, *Candida albicans* TIMM 1768, held by the Teikyo University Medical Mycology Research Center was used as the *Candida*. This *Candida* was cultured for 20 hours at 37° C. on a Sabouraud Dextrose Agar culture plate. The multiplied bacterial cells were recovered, and then suspended in sterilized water so as to form *Candida* solutions whose bacterial count was adjusted to 5×103 cells/ml. Each sample was dissolved in advance in DMSO (dimethyl sulfoxide) so as to match the final concentration, and was then added to a ⅓ RPMI-1640 culture medium containing 2% calf serum so as to form sample solutions. 100 μL of both the sample solution (having a DSMO concentration in the culture medium of 0.5%) and the *Candida* bacterial solution were then placed respectively in each well of a 96-hole microplate (manufactured by Sumitomo Bakelite, Tokyo), and these were then cultured for three hours at 37° C. in a 5% carbon dioxide gas atmosphere. After three hours, the solutions in each well were discarded and the wells were cleaned. Subsequently, 200 μL of ⅓ RPMI-1640 was newly added to each well, and culturing was performed for 16 hours at 37° C. in a presence of 5% carbon dioxide gas. Once this culturing had ended, the solutions in each well were removed by suction, and the wells were washed using physiological saline. 200 μL of 70% ethanol was then injected so as to sterilize the *Candida*. After the ethanol had been removed, and the wells washed with tap water, 100 μL of a dye solution (i.e., a 0.1 M phosphate buffer containing 0.01% of dissolved crystal violet solution) was injected and left standing for 15 minutes. As a result, the *Candida* mycelia adhering to the surface of the wells were dyed.

After the wells were then washed with tap water so as to remove excess dye solution, 150 μL of 3-isopropanol containing 0.04 NHCL, and 50 μL of a 0.25% sodium dodecyl sulfate solution were then injected so as to free the coloring adhering to the bacterial cells. After the coloring had been freed, the plate was set in a multiscan photometer (i.e., a Multiskan FC, manufactured by Thermo Fisher Scientific Inc.), and the OD at 620 nm was measured in each well. The growth inhibition rate was then determined using the following formula.

Growth inhibition rate (%)=(1—sample $OD$/subject $OD$)×100

Figure 2:
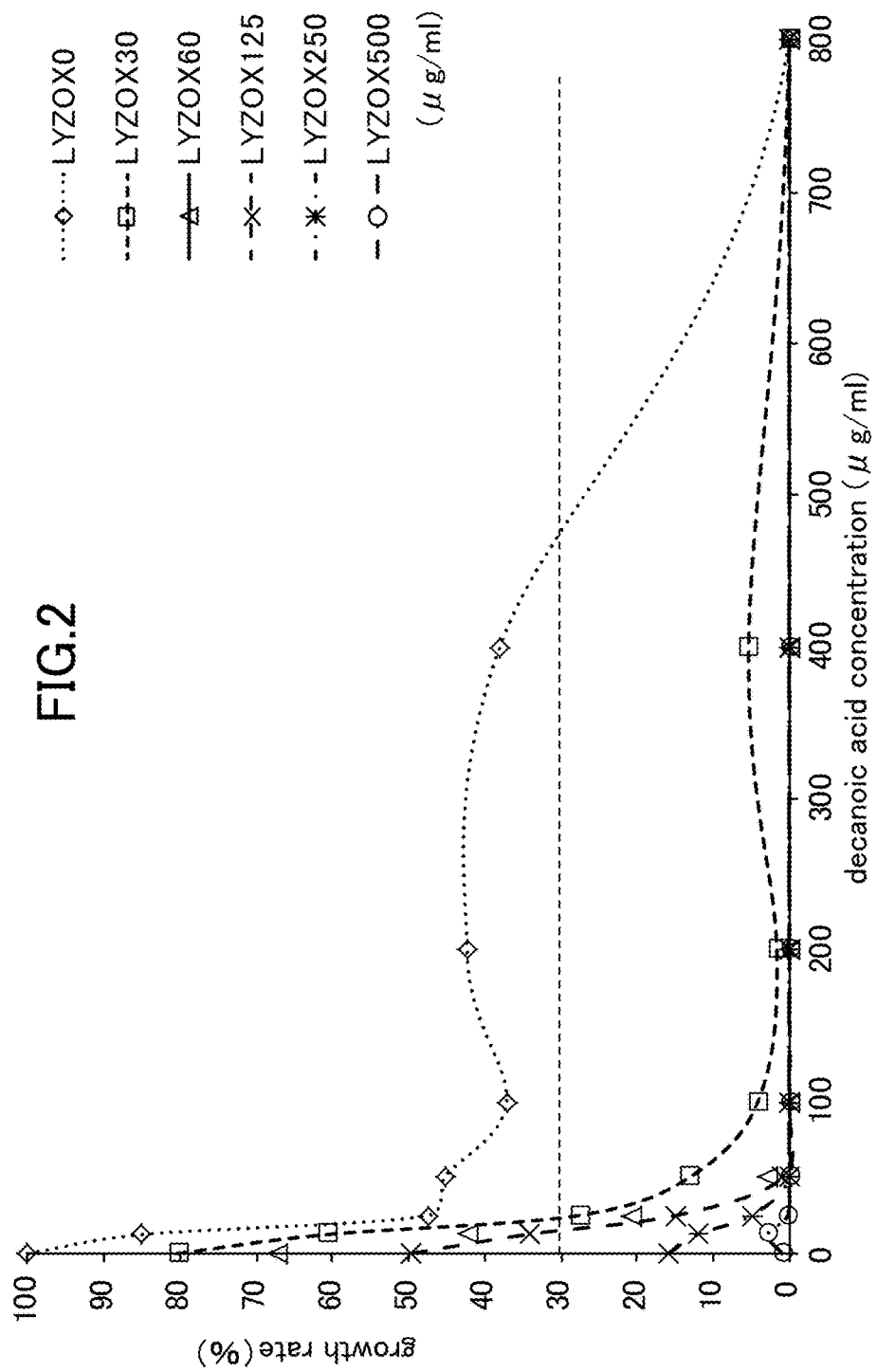
FIG. 2 is a view showing Candida growth rates when a lysozyme-chitosan complex is used in combination with decanoic acid.

As is shown in FIG. 1 and FIG. 2, an IC 70 (i.e., a 70% growth inhibitory concentration) of each of the LYZOX, terpinen-4-ol, and decanoic acid were as follows.

| LYZOX (alone) | 193 μg/ml |
| Terpinen-4-ol (alone) | 1900 μg/ml |
| Capric acid (Decanoic acid) (alone) | 480 μg/ml |

[Example 2] Synergistic Effect in Anticandidal Activity Against *Candida* Mycelial Growth Obtained from Combination of LYZOX with terpinen-4-ol or Decanoic Acid Generally, the definition of a synergistic effect when antibacterial substances are used in combinations against microorganisms is an effect that is significantly greater than the sum of the individual effects of two agents. As is described below, the evaluation of a synergistic effect can be performed by means of a checkerboard method using an FIC index (Fractional Inhibitory Concentration index) determined from the MIC values of two agents. Namely, it is determined that a synergistic effect exists when the FIC index is less than 0.5.
(How to Determine an FIC Index)

FIC index=$A_1/A_0+B_1/B_0$ $A_0$: MIC of A agent alone
$A_1$: MIC of A agent when A agent is used in combination with B agent
$B_0$: MIC of B agent alone
$B_1$: MIC of B agent when A agent is used in combination with B agent (Evaluation of Effect of Combined Use Obtained from FIC Index)

| FIC < 0.5 | Synergistic effect |
|---|---|
| 0.5 < FIC < 1.0 | Extreme synergistic effect |
| FIC = 1.0 | Synergistic effect |
| 1.0 < FIC = 2.0 | N/A |
| FIC > 2.0 | Antagonistic action |

The anticandidal activity synergistic effect provided by the combined use was evaluated using a checkerboard method. A hypothetical checkerboard was placed on top of the 96-hole microplate, and concentration series of each of the terpinen-4-ol or decanoic acid and the LYZOX were made to mutually intersect. The experiment conditions and the measurement method and the like were the same as those employed for the mycelial growth test (i.e., Example 1).

When LYZOX was used in combination with terpinen-4-ol, as is shown in FIG. 1, the IC (at a 70% growth inhibitory concentration) of the LYZOX and terpinen-4-ol were as follows.

| LYZOX (used in combination) | 60 µg/ml |
|---|---|
| Terpinen-4-ol (used in combination) | 280 µg/ml |

In other words, when LYZOX and terpinen-4-ol were used in combination, the FIC index with respect to the mycelial growth of the *Candida* was 0.447, and it was therefore determined that a synergistic effect existed.

When LYZOX was used in combination with capric acid (decanoic acid), as is shown in FIG. 2, the IC (at a 70% growth inhibitory concentration) of the LYZOX and capric acid (decanoic acid) were as follows.

| LYZOX (used in combination) | 30 µg/ml |
|---|---|
| Capric acid (Decanoic acid) (used in combination) | 25 µg/ml |

In other words, when LYZOX and capric acid were used in combination, the FIC index with respect to the mycelial growth of the *Candida* was 0.208, and it was therefore determined that a synergistic effect existed.

[Example 3] Therapeutic Effect Obtained from Combination of LYZOX with terpinen-4-ol in an Oral Candidiasis Model in Mice Using ICR strain mice (males, 6 weeks old, Charles River Laboratories, Japan) as the experimental animals, these mice were subcutaneously injected with 100 mg/kg of prednisolone as an immunosuppressant on the day prior to the candidiasis inoculation. Additionally, tap water containing 15 mg/ml of chlortetracycline hydrochloride was made freely available starting from that same day. On the day of the innoculation, in order to keep the mice in a resting state, 14.4 mg/kg of chlorpromazine hydrochloride (manufactured by Wako Pure Chemical Industries, Ltd.) was intramuscularly administered in advance. The bacterial strain and culturing method that were used were the same as in the Examples as far as the previous paragraph, and the multiplied bacterial cells were suspended in an RPMI-1640 culture medium containing 2% calf serum so as to form a bacterial solution whose bacterial count was adjusted to $2 \times 10^8$ cells/ml. A cotton bud was then soaked in this bacterial solution, and then rubbed inside the oral cavity of the resting mice so as to inoculate the mice with the *Candida* bacteria.

The samples in the table below were administered to the oral candidiasis mice in the following manner. Firstly, the samples were suspended in advance in distilled water using Tween 80 (having a final concentration of 1%), and then 3, 24, and 27 hours after the candidiasis inoculation, using a gastric tube for mice, droplets thereof were administered onto the tongue dorsum inside the oral cavity. Two days after the inoculation the mouse was euthanized, and the tongue symptom score was evaluated in accordance with a reference. The interior of the oral cavity of each mouse was then wiped with a cotton bud, and the *Candida* bacterial cells recovered by that cotton bud were suspended in a saline solution. A fixed quantity of this was then coated onto a *Candida* GS agar plate, and was cultured at 37° C. for 20 hours. The number of colonies appearing after this time was then measured. The number of viable *Candida* bacteria CFU (colony forming units) recovered from the relevant individuals was then calculated from the number of colonies.

TABLE 1

| No. | Group | Infection | Inoculation sample | Number of mice |
|---|---|---|---|---|
| 1 | Negative control group | + | FLCZ 10 mg/ml | 3 |
| 2 | Positive control group | + | Water | 3 |
| 3 | LYZOX only group | + | L 20 mg/ml | 3 |
| 4 | Terpinen-4-ol only group | + | T 10 mg/ml | 3 |
| 5 | LYZOX + Terpinen-4-ol group | + | 10 mg/ml | 3 |
| 6 | Non-infected group | − | Water | 3 |

Figure 3:
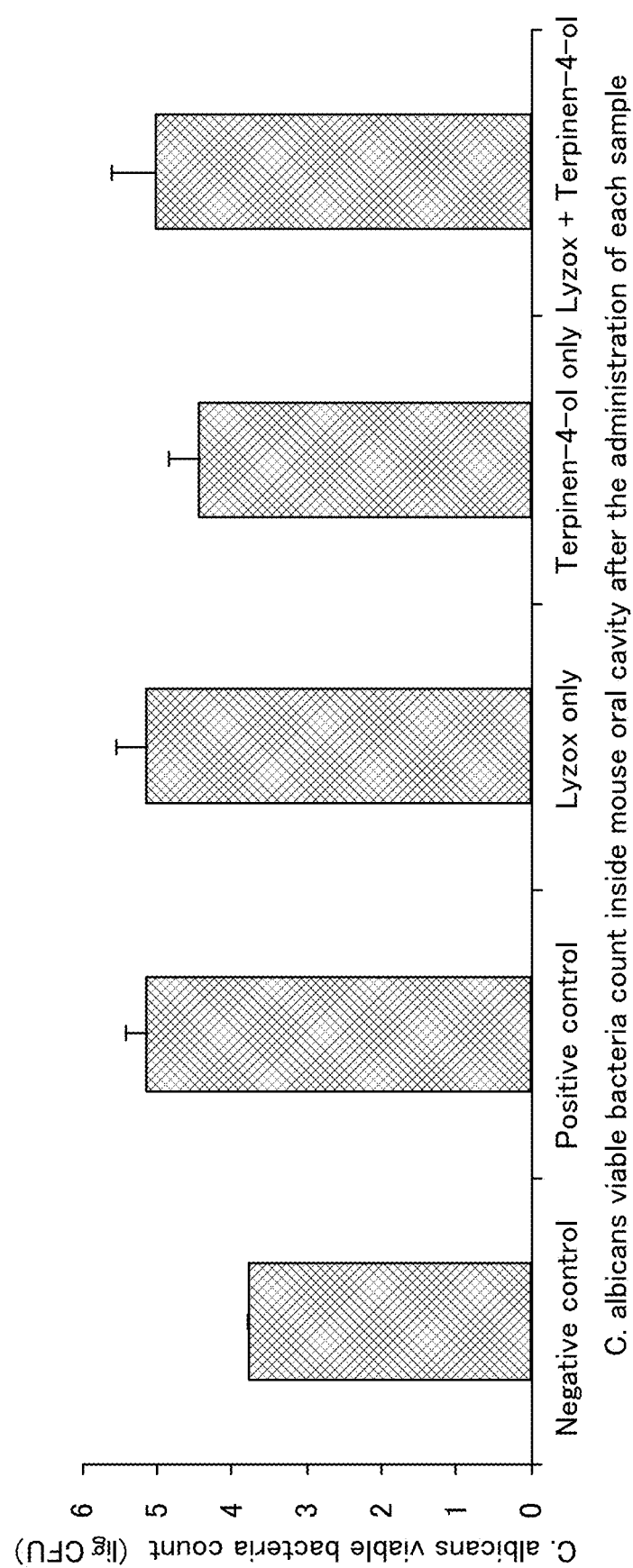
FIG. 3 is a view showing results when a viable bacteria count inside an oral cavity that is obtained when a lysozyme-chitosan complex is used in combination with terpinen-4-ol is measured in an oral candidiasis model in mice.
Figure 4:
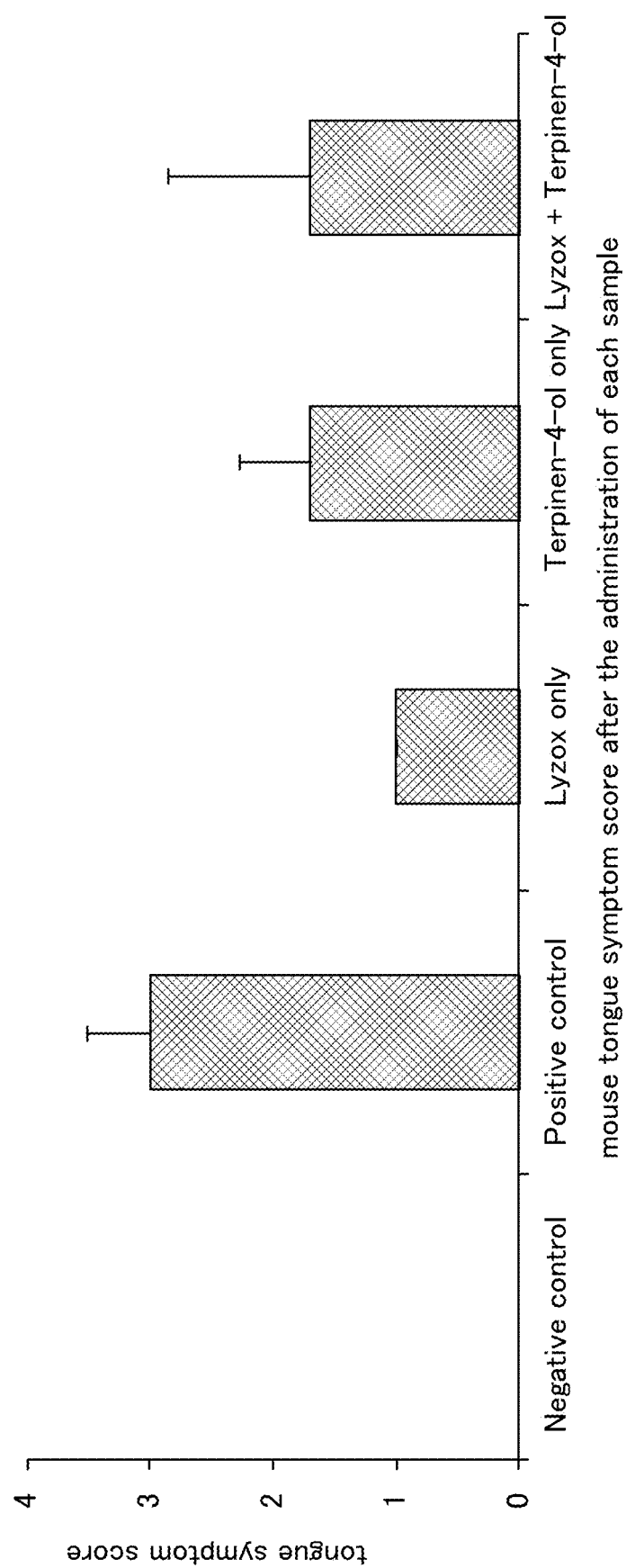
FIG. 4 is a view showing a tongue symptom score obtained when a lysozyme-chitosan complex is used in combination with terpinen-4-ol in an oral candidiasis model in mice.

As is shown in FIG. 3, the results of this experiment showed that a reduction in the viable bacterial count in the terpinen-4-ol only group was recognized for the viable bacteria count recovered from the oral cavity. Moreover, as is shown in FIG. 4, a remarkable improvement effect was recognized in the tongue symptom score in the LYZOX only group.

[Example 4] Anticandidal Activity Effect Obtained from Simple Lysozyme, Simple Chitosan, a Lysozyme-Chitosan Blend, and a Combination of LYZOX with terpinen-4-ol Against *Candida* Mycelial Growth The anticandidal activity synergistic effect obtained from a combined use was evaluated using a checkerboard method in the same way as in Example 2. A hypothetical checkerboard was placed on top of a 96-hole microplate, and concentration series of each of the simple lysozyme, the simple chitosan, the lysozyme-chitosan blend, and the combination of LYZOX with terpinen-4-ol were made to mutually intersect. The experiment conditions and the measurement method and the like were the same as those employed for the mycelial growth test (i.e., Example 1).

Figure 5:
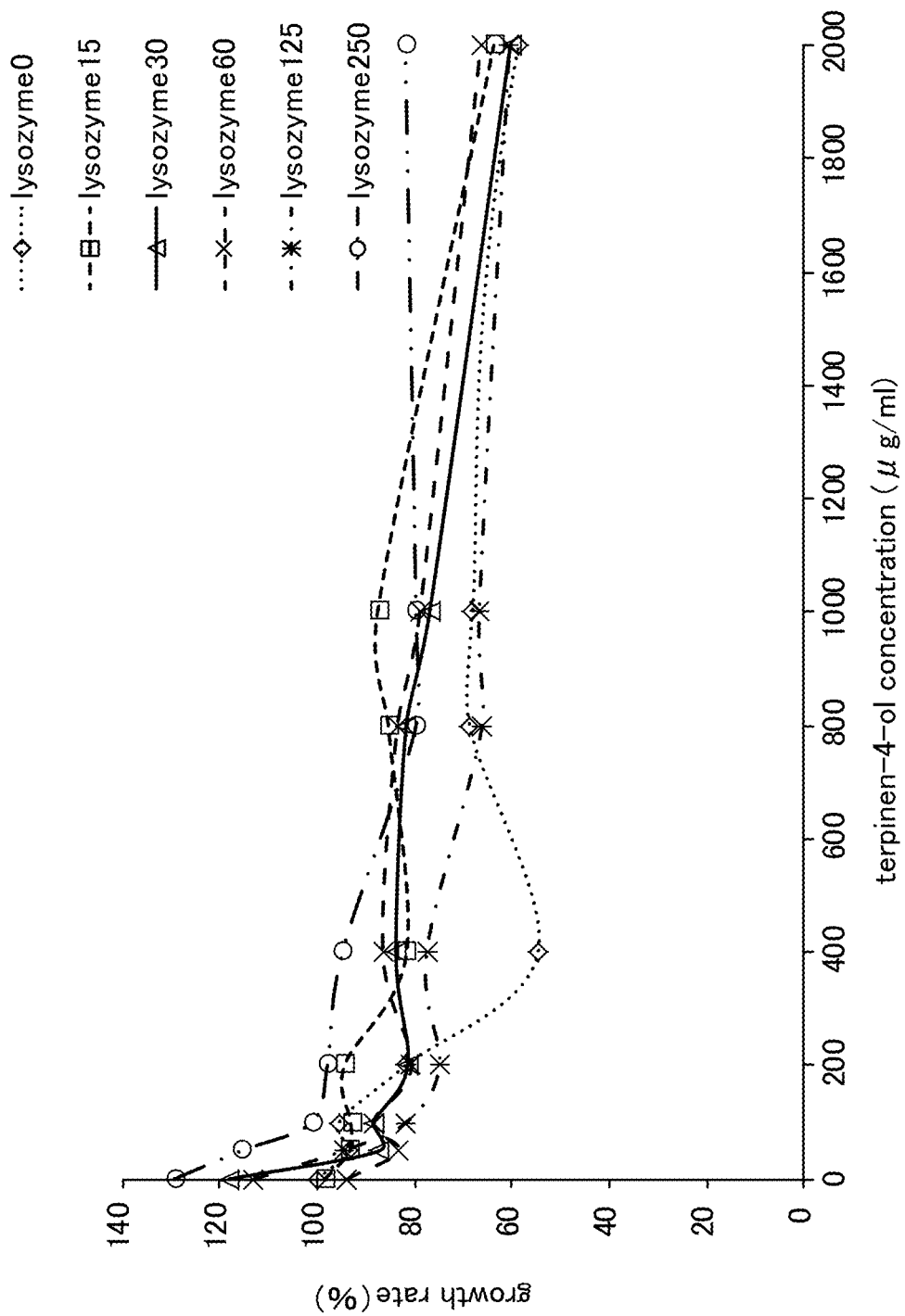
FIG. 5 is a view showing Candida growth rates when lysozyme is used in combination with terpinen-4-ol.
Figure 6:
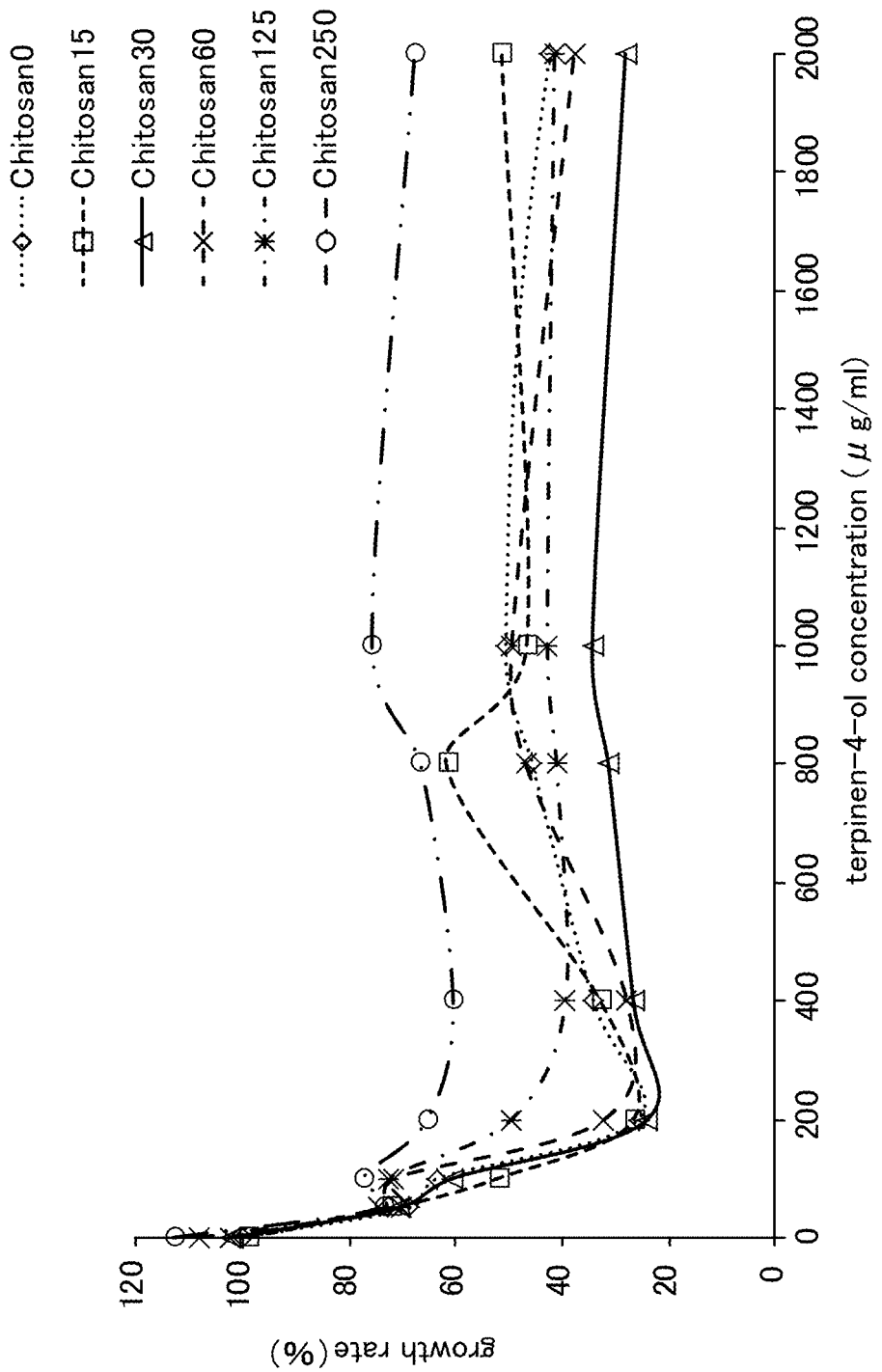
FIG. 6 is a view showing Candida growth rates when chitosan is used in combination with terpinen-4-ol.
Figure 7:
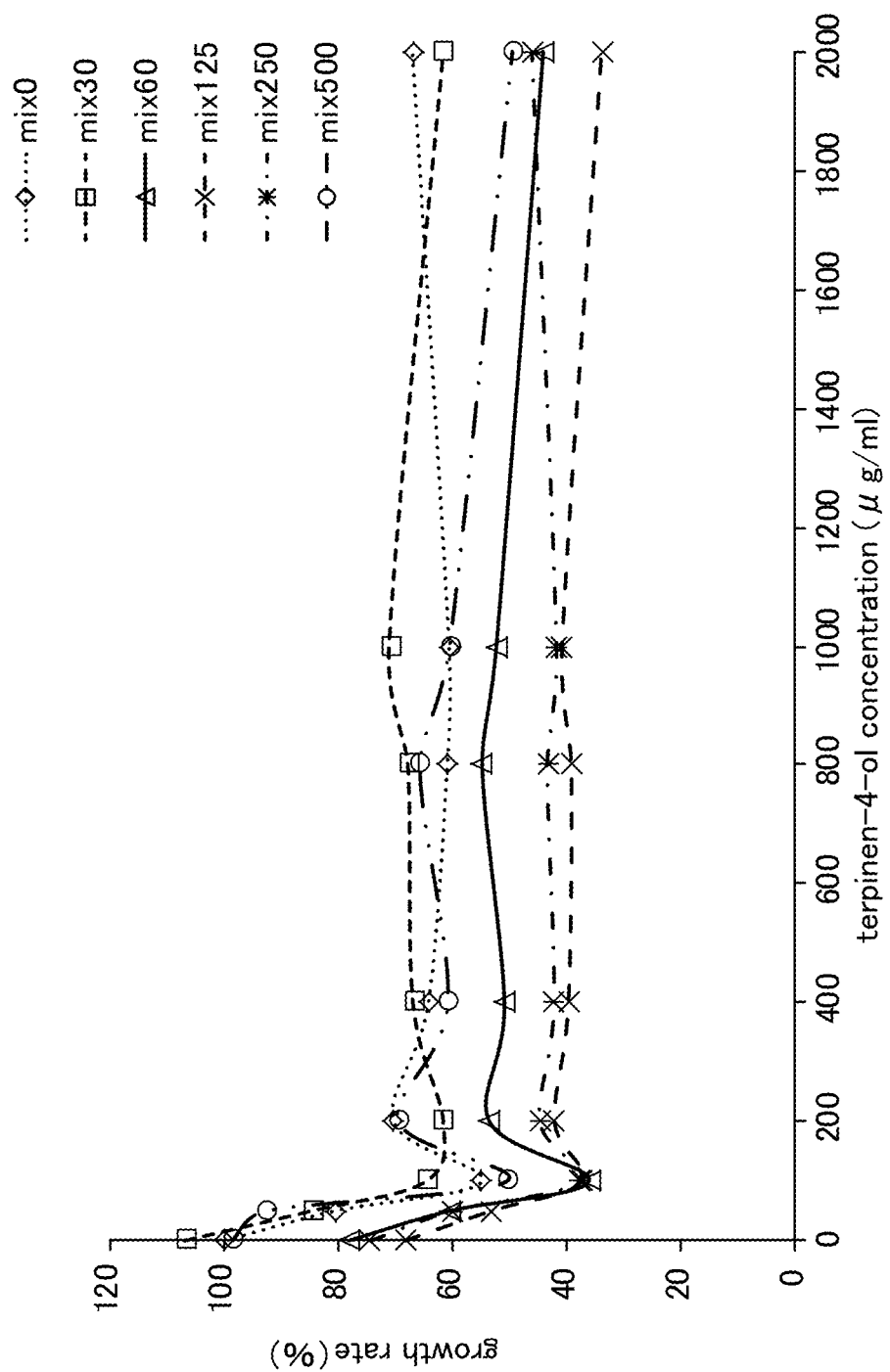
FIG. 7 is a view showing Candida growth rates when a lysozyme-chitosan blend is used in combination with terpinen-4-ol.

As is shown in FIG. 5 through FIG. 7, the experiment results showed that when simple lysozyme was used in combination with terpinen-4-ol, when simple chitosan was used in combination with terpinen-4-ol, and when a mixture of lysozyme with chitosan was used in combination with terpinen-4-ol, then no improvement effect in the anticandidal activity obtained from a combined usage against *Candida* mycelial growth was seen. In contrast, as is shown in FIG. 1, when LYZOX was used in combination with terpinen-4-ol, then compared with the three patterns of combined use described above, a remarkable improvement effect was recognized.

[Example 5] Anticandidal Activity Effect Obtained from Simple Lysozyme, Simple Chitosan, a Lysozyme-Chitosan Blend, and a Combination of LYZOX with Decanoic Acid Against *Candida* Mycelial Growth The anticandidal activity synergistic effect obtained from a combined use was evaluated using a checkerboard method in the same way as in Example 2. A hypothetical checkerboard was placed on top of a 96-hole microplate, and concentration series of each of the simple lysozyme, the simple chitosan, the lysozyme-chitosan blend, and the combination of LYZOX with decanoic acid were made to mutually intersect. The experiment conditions and the measurement method and the like were the same as those employed for the mycelial growth test (i.e., Example 1).

Figure 8:
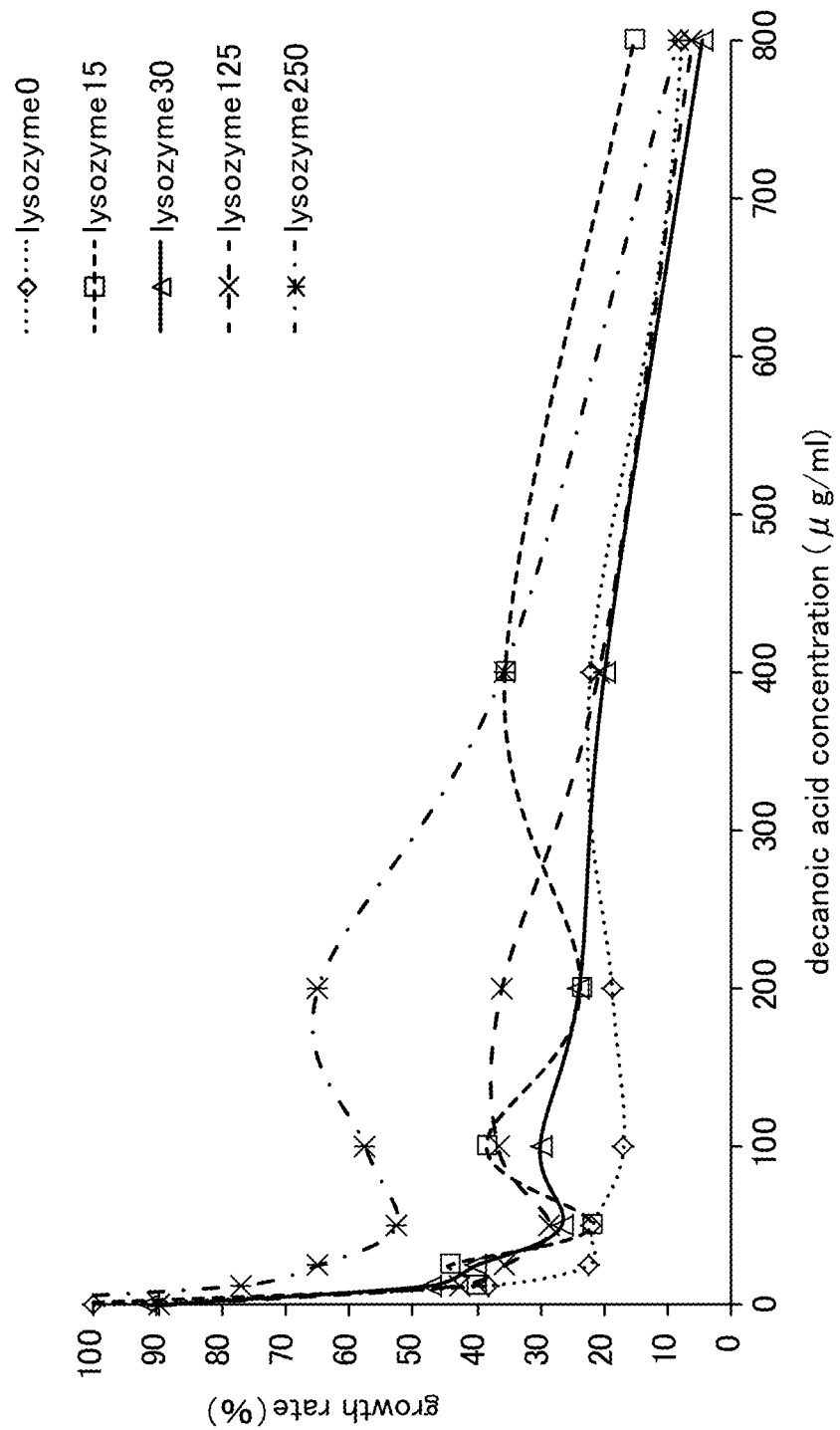
FIG. 8 is a view showing Candida growth rates when lysozyme is used in combination with decanoic acid.
Figure 9:
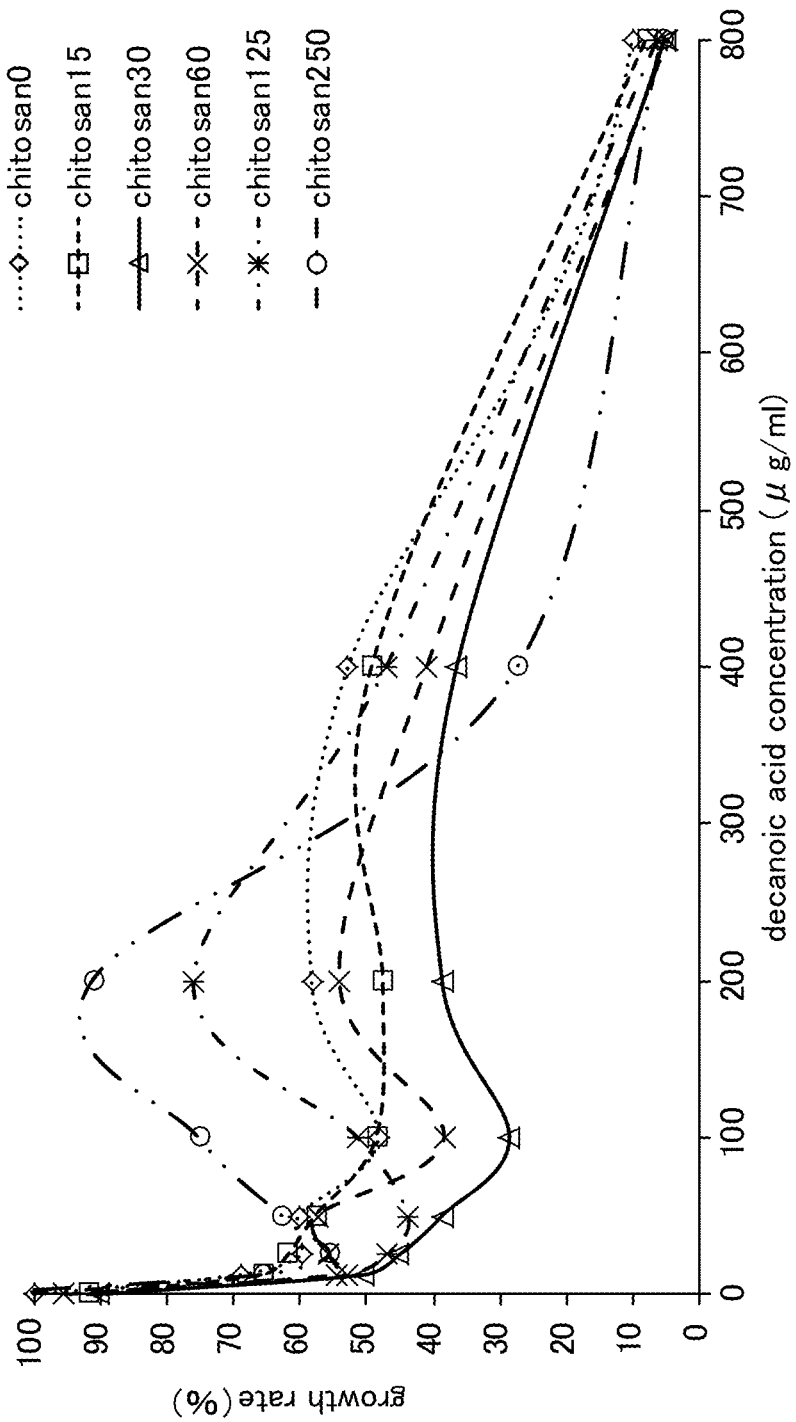
FIG. 9 is a view showing Candida growth rates when chitosan is used in combination with decanoic acid.
Figure 10:
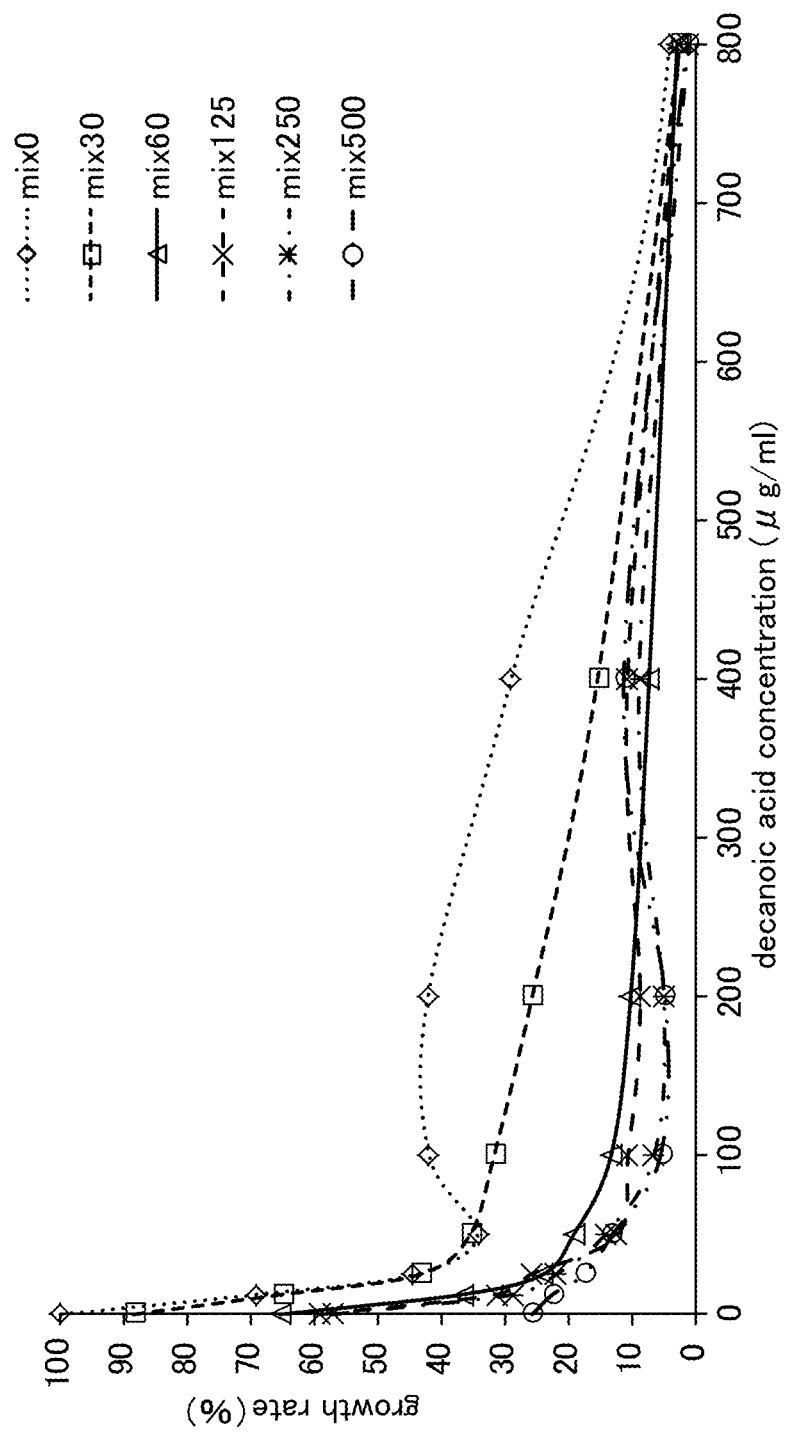
FIG. 10 is a view showing Candida growth rates when a lysozyme-chitosan blend is used in combination with decanoic acid.

As is shown in FIG. 8 through FIG. 10, the experiment results showed that when simple lysozyme was used in combination with decanoic acid, when simple chitosan was used in combination with decanoic acid, and when a mixture of lysozyme with chitosan was used in combination with decanoic acid, then no improvement effect in the anticandidal activity obtained from a combined usage against *Candida* mycelial growth was seen. In contrast, as is shown in FIG. 2, when LYZOX was used in combination with decanoic acid, then compared with the three patterns of combined use described above, a remarkable improvement effect was recognized.

[Example 6] Anticandidal Activity Effect Obtained from Simple Lysozyme, Simple Chitosan, a Lysozyme-Chitosan Blend, and LYZOX Against *Candida* Mycelial Growth The anticandidal activity effect obtained from each test reagent was evaluated using a checkerboard method in the same way as in Example 2. A hypothetical checkerboard was placed on top of a 96-hole microplate, and concentration series of each of the simple lysozyme, the simple chitosan, the lysozyme-chitosan blend, and the LYZOX were prepared. The experiment conditions and the measurement method and the like were the same as those employed for the mycelial growth test (i.e., Example 1).

Figure 11:
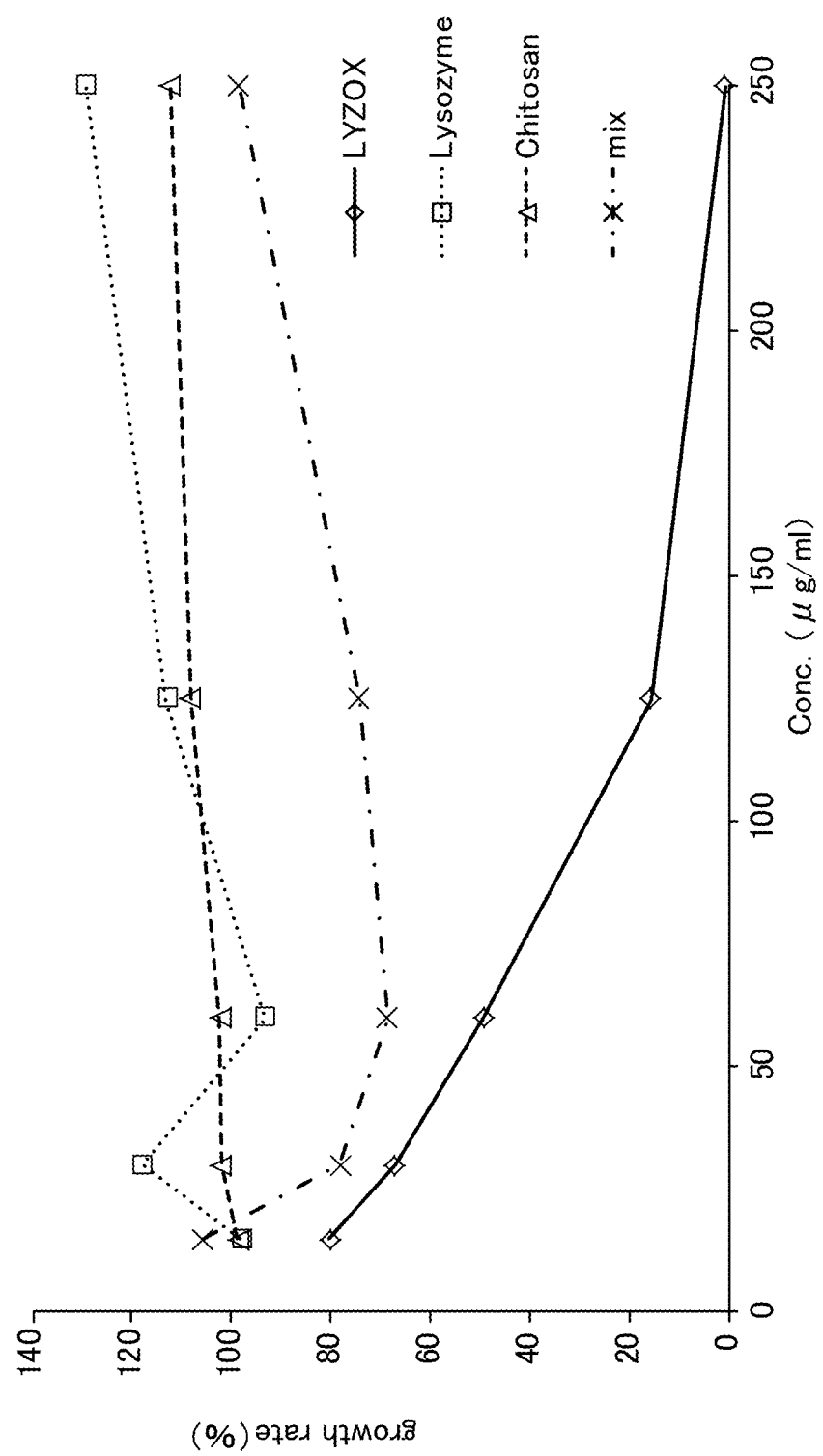
FIG. 11 is a view showing Candida growth rates at various concentrations of simple lysozyme, simple chitosan, a lysozyme-chitosan blend, and a lysozyme-chitosan complex.

As is shown in FIG. 11, the experiment results showed that when simple lysozyme was used and when simple chitosan was used, no improvement effect in the anticandidal activity against *Candida* mycelial growth was seen. Moreover, when a mixture of lysozyme with chitosan (MIX) was used, although an improvement effect in the anticandidal activity against *Candida* mycelial growth was visible, it was seen that the anticandidal activity effect gradually reduced as the concentration increased. In contrast, when LYZOX was used, an improvement effect in the anticandidal activity against *Candida* mycelial growth was visible, and it was seen that the anticandidal activity effect gradually increased as the concentration increased. In particular, when the LYZOX concentration was 250 µg/ml, the growth rate dropped to almost zero (actually, 0.9%).

[Example 7] Anti-*Malassezia*Fungal Activity Effect Obtained from Ketoconazole, and from a Complex of Lysozyme and Chitosan Against *Malassezia*Fungi (*Malassezia pachydermatis*)

In the *Malassezia*sensitivity test, 100 µL lots of a test bacterial solution adjusted to McFarland 1.0 were coated over an Agar plate using an MLNA culture medium (the composition of which is shown in Table 2). Sterile paper disks having a paper thickness of 8 mm which are used for inspecting antibiotics were placed on a Petri dish, and 50 µL of each test sample was dripped onto these paper disks. After the test samples had subsequently been cultured for seven days at 32° C., they were observed and their properties were determined. In addition, the diameter of the zone of inhibition was measured. Note that 0.5% DMSO, ketoconazole 10 µg/ml, ketoconazole 100 µg/ml, LYZOX 5 mg/ml, LYZOX 10 mg/ml, LYZOX 20 mg/ml, and LYZOX 40 mg/ml were used as the test samples.

MLNA Culture medium 25 ml/plate

TABLE 2

| | |
|---|---|
| Bacto Peptone | 5 g |
| Glucose | 5 g |
| Yeast extract | 1 g |
| Oxbile desiccated | 4 g |
| Glycerol | 5 ml |
| Glycerol monostearate | 0.25 g |
| Tween60 | 2.5 ml |
| Agar | 7.5 g |
| DW | 500 ml |
| Chloramphenicol | 0.0125 g |

The test samples were placed in an autoclave at 110° C. for 20 minutes.

Results for the Malasseziazone of inhibition (mm) of each test sample are shown below.

TABLE 3

| | Diameter of zone of inhibition (mm) | |
|---|---|---|
| Test sample (50 µl) | Exp. 1 | Exp. 2 |
| DW | 0 | 0 |
| 0.5% DMSO | 0 | 0 |
| Ketoconazole 10 µg/ml | 11 × 12 | — |
| Ketoconazole 100 µg/ml | 27 × 28 | 24 × 24 |
| LYZOX 5 mg/ml | — | 10 × 11 |
| LYZOX 10 mg/ml | 16 × 16 | 14 × 15 |
| LYZOX 20 mg/ml | 21 × 21 | — |
| LYZOX 40 mg/ml | 24 × 24 | — |

Figure 12:
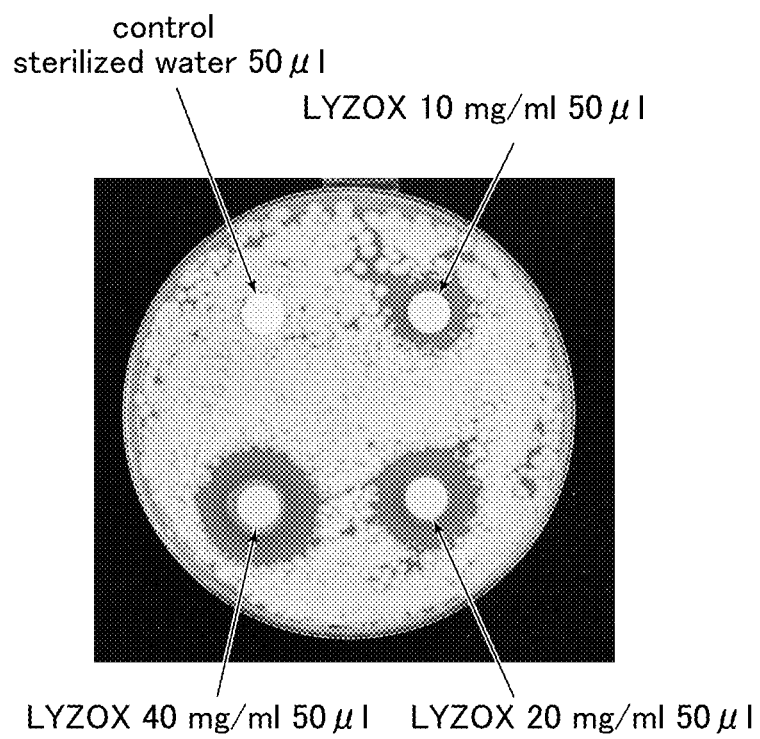
FIG. 12 is a photograph showing a zone of inhibition of a lysozyme-chitosan complex against Malassezia fungi.

As is shown in FIG. 12, in Exp. 1, a zone of inhibition of 16×16 mm (on a paper disk of 8 mm) was visible around the paper disk onto which 50 µl of LYZOX 10 mg/ml had been dripped. In the same way, a zone of inhibition of 21×21 mm was visible around the paper disk onto which 50 µl of LYZOX 20 mg/ml had been dripped, and a zone of inhibition of 24×24 mm was visible around the paper disk onto which 50 III of LYZOX 40 mg/ml had been dripped. No zone of inhibition was visible for the sterilized water of the control.

In Exp. 2, a zone of inhibition of 14×15 mm was visible around the paper disk onto which 50 µl of LYZOX 10 mg/ml had been dripped, and a zone of inhibition of 10×11 mm was visible around the paper disk onto which 50 µl of LYZOX 5 mg/ml had been dripped.

Example 8

The anti-*Malassezia* fungal activity obtained from LYZOX against *Malassezia* fungi (*Malassezia pachydermatis*) was evaluated using an agar dilution method. Specifically, an agar plate (having the same composition as that described above in Table 2) was prepared using MLNA culture mediums to which the LYZOX LIZOX and other samples had been added so as to attain the respective concentrations (final concentrations) given in Table 2 (see above). 100 µL lots of the test bacterial solution adjusted to McFarland 1.0 were coated over this Agar plate and were cultured for seven days at 32° C. Thereafter, the growth rate of the bacteria thereon were compared with a control (i.e., an MLNA culture medium containing no test additives) and their properties were determined.

Figure 13:
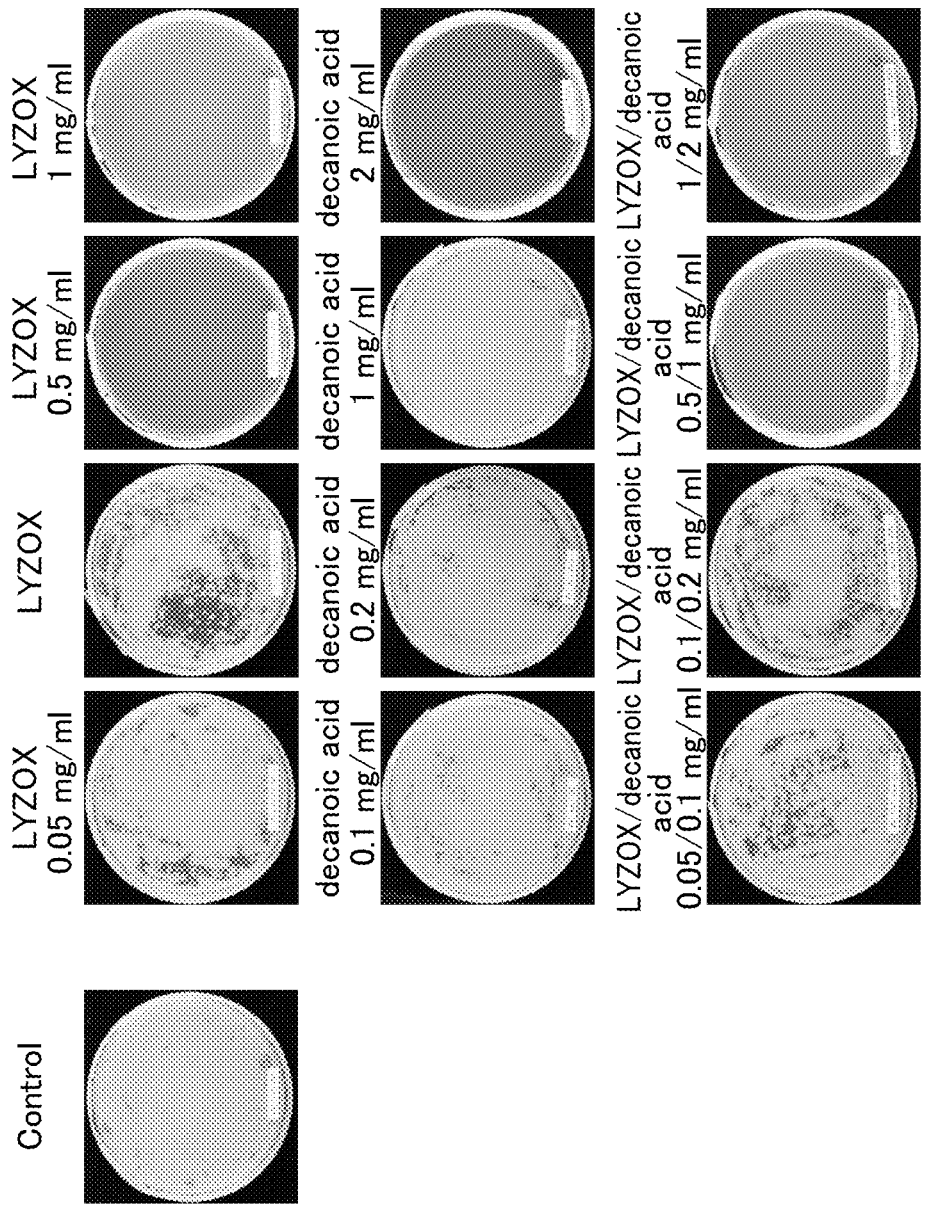
FIG. 13 is a photograph showing states after seven days of colony formation of Malassezia fungi in respective test samples.
Figure 14:
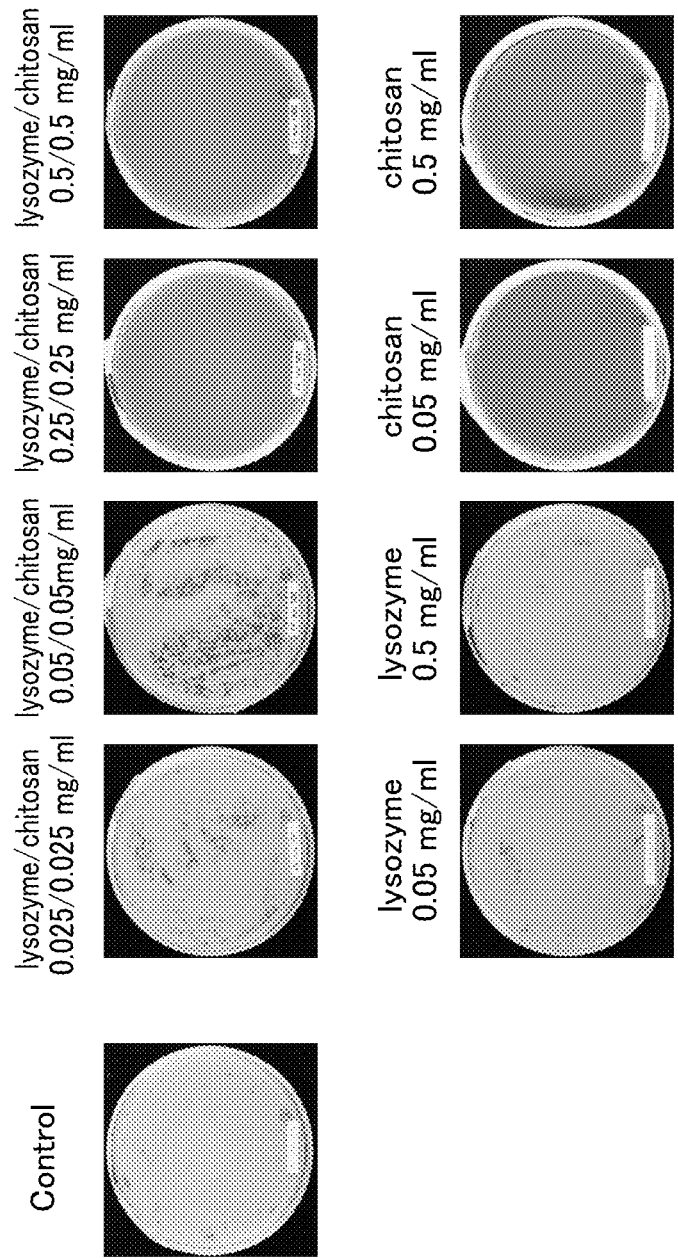
FIG. 14 is a photograph showing states after seven days of colony formation of Malassezia fungi in respective test samples.

Results for the negativity and positivity of the bacteria obtained from each test sample are shown below. Note that if the mycelial growth rate of the control is taken as 100%, then when the mycelial growth rate in the test sample is 0%, this is determined to be [−], while if the mycelial growth rate in the test sample is 1~20%, this is determined to be [+], and if the mycelial growth rate in the test sample is 21~90%, this is determined to be [+++]. The state of colony formation of the bacteria in each test sample is shown in FIG. 13 and FIG. 14. Note that FIG. 13 and FIG. 14 are photographs showing states 7 days after colony formation of the *Malassezia* fungi in each test sample.

TABLE 4

| Sample name | Concentration (mg/ml) | Determination |
|---|---|---|
| LYZOX | 1 | − |
|  | 0.5 | − |
|  | 0.1 | ++ |
|  | 0.05 | +++ |
| Decanoic acid | 2 | + |
|  | 1 | +++ |
|  | 0.2 | +++ |
|  | 0.1 | +++ |
| LYZOX/ | 1/2 | − |
| Decanoic acid | 0.5/1 | − |
|  | 0.1/0.2 | ++ |
|  | 0.05/0.1 | ++ |
| Lysozyme | 0.5 | +++ |
|  | 0.05 | +++ |
| Chitosan | 5 | − |
|  | 0.05 | − |
| Lysozyme/ | 0.5/0.5 | − |
| Chitosan | 0.25/0.25 | − |
|  | 0.05/0.05 | ++ |
|  | 0.025/0.025 | ++ |

| Mycelial growth rate taking control as 100 | Determination |
|---|---|
| 0% | − |
| 1 to 20% | + |
| 21 to 90% | ++ |
| 91 to 100% | +++ |

From the results of this experiment the growth inhibitory concentrations in each sample were found to be as follows.

TABLE 5

| Sample name | Growth inhibitory concentration (mg/ml) |
|---|---|
| LYZOX | 0.5 |
| Decanoic acid | — |
| LYZOX/Decanoic acid | 0.5/1 |
| Lysozyme | — |
| Chitosan | 0.05 |
| Lysozyme/Chitosan | 0.5/0.5 |

From the above-described experiments, it was found that LYZOX alone exhibited anti-Malasseziafungal activity against Malassezia fungi. Furthermore, it was found that LYZOX used in combination with decanoic acid also exhibited anti-Malasseziafungal activity, however, no improvement effect compared with the LYZOX alone was found. It may be considered that the fact that Malassezia fungi are a perfect yeast type of fungus causes the anti-bacterial effects thereof to be different from those of other types of fungus.

[Example 9] Anti-*Trichophyton* Activity of LYZOX and Decanoic Acid Against *Trichophyton*, and Synergistic Effect of Anti-*Trichophyton* Activity Obtained by Using these in Combination In the same way as in the test for *Candida*, methods of performing an in vitro inhibition test for *Trichophyton* are well-established, and as a result, the MIC (minimum inhibitory concentration) of various types of material can be measured.

A clinical isolate, *Trichophyton mentagrophytes* TIMM 2789, held by the Teikyo University Medical Mycology Research Center was used as the *Trichophyton*. For the preculture process, this *Trichophyton* was extracted from low-temperature silica stock one week prior to the day of the test, and was cultured on a Sabouraud Dextrose Agar culture plate containing 50 µg/ml of chloramphenicol and 500 µg/ml of cycloheximide (such that these components were diluted to 1/10). This culturing was performed for one week at 28° C., and the bacteria were collected and used on the day of the test. The setting of the *Trichophyton* bacterial count was achieved by transferring the collected bacteria using a pour-plate method to a culture medium such that the final concentration was $10^3$ cells/ml. In addition, the respective test samples were also transferred to a culture medium using a pour-plate method such that the final concentrations thereof were set to those shown in the table below. An RPMI culture medium (diluted to a final concentration of 1/3) containing a bacterial solution adjusted with 1.5% agar was also held at 37° C. so that it did not solidify during the preparation process. In the preparation, 1 ml of each test sample solution and 24 ml of RPMI-1640 culture medium were blended together, and prepared in a sterilized plastic Petri dish. The *Trichophyton* inoculation culture medium that was prepared in this manner was then cultured at 28° C. for four days, and the growth inhibitory effect of the mycelia after this culturing was observed and the properties thereof determined. The determinations were made both visually, and in the case of turbidity being present, by comparing the growth condition of the mycelia with a control (containing no test sample additives) via photomicrograph (at magnification ×40).

Figure 15:
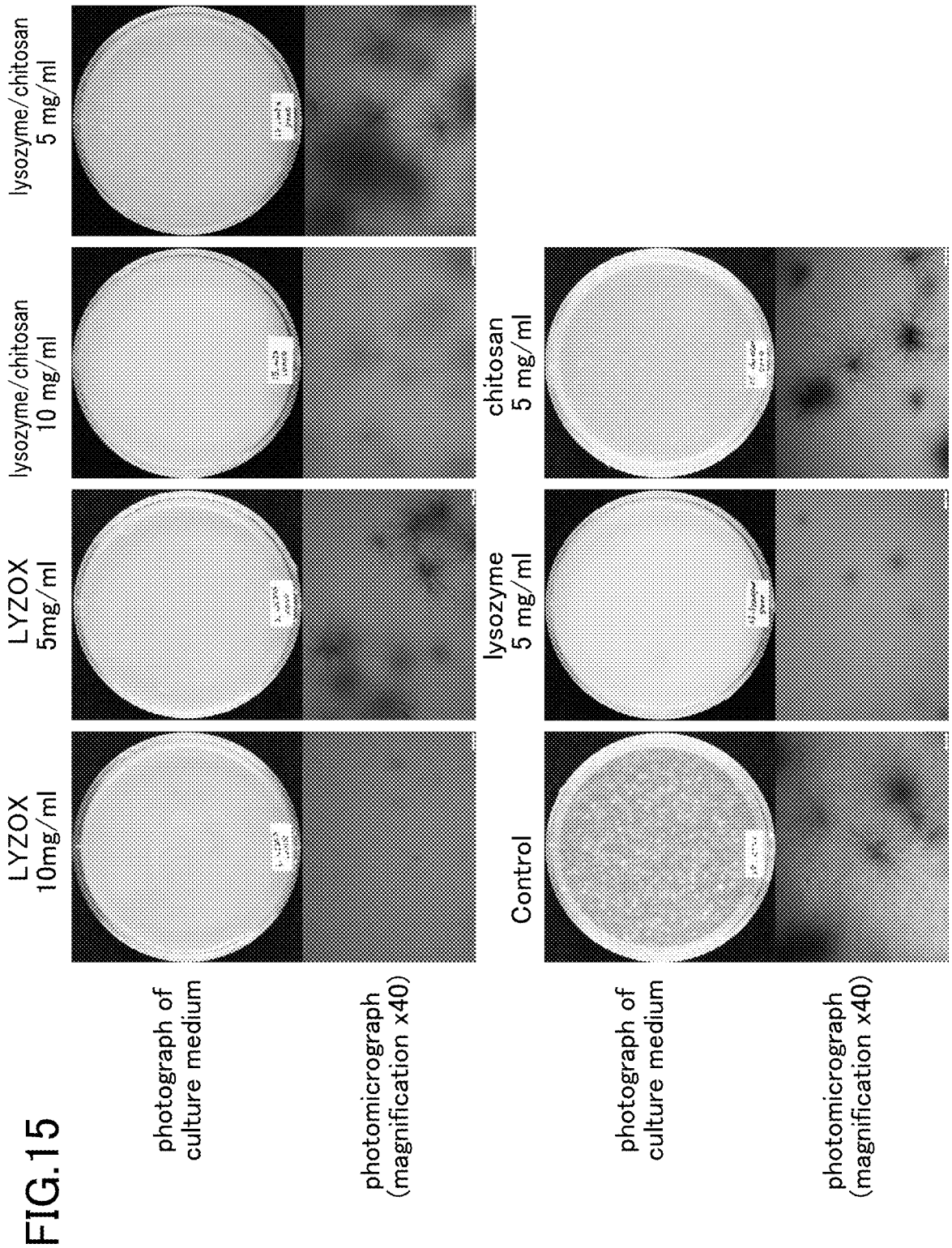
FIG. 15 is a photograph showing states after seven days of colony formation of Trichophyton in respective test samples.
Figure 16:
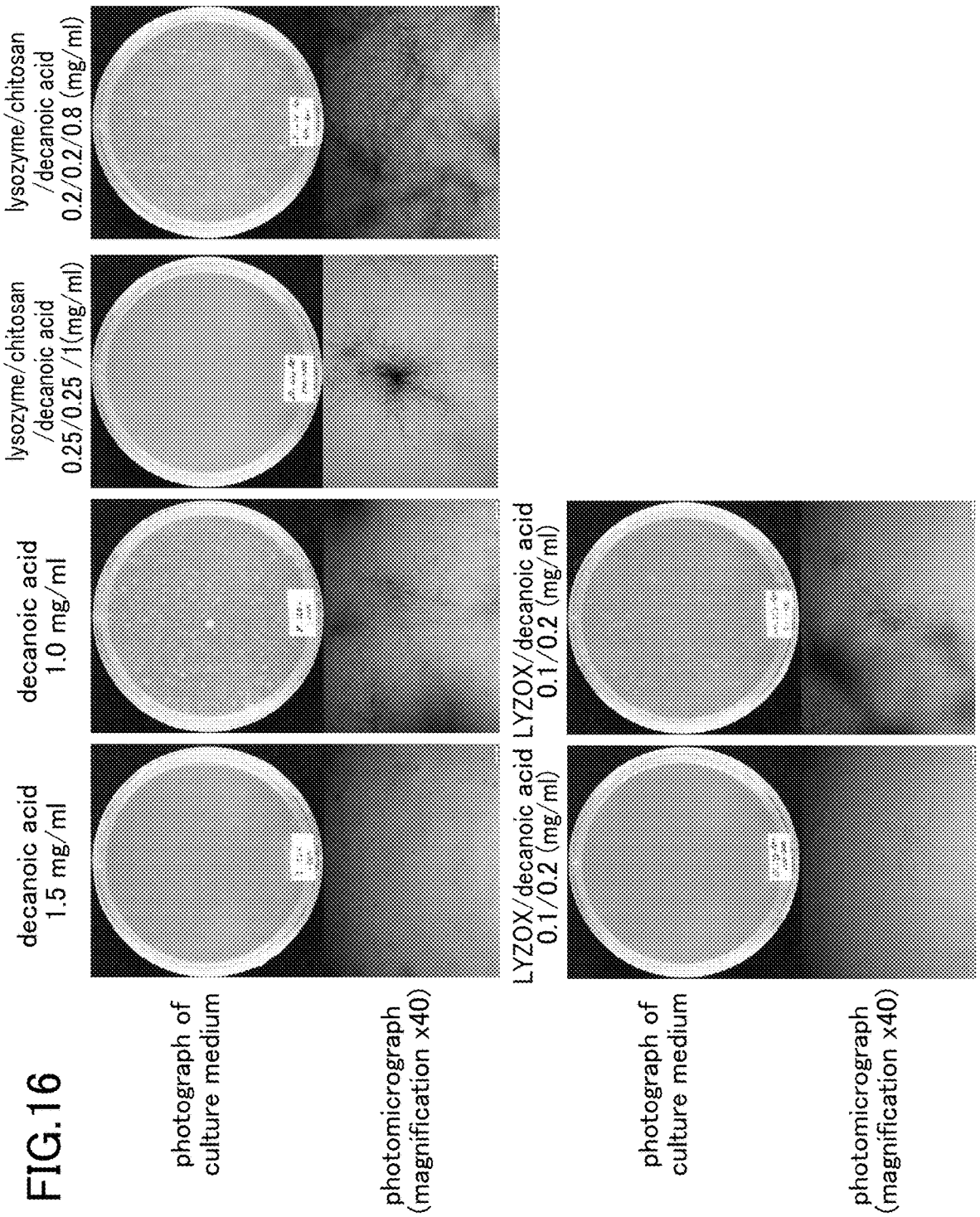
FIG. 16 is a photograph showing states after seven days of colony formation of Trichophyton in respective test samples.

Results for the negativity and positivity of the bacteria obtained from each test sample are shown below in Table 6. Note that if the mycelial growth rate of the control is taken as 100%, then when the mycelial growth rate in the test sample is 0%, this is determined to be [−], while if the mycelial growth rate in the test sample is 21~20%, this is determined to be [+], and if the mycelial growth rate in the test sample is 21~90%, this is determined to be [+++]. The state of colony formation of the bacteria in each test sample is shown in FIG. 15 and FIG. 16. Note that FIG. 15 and FIG. 16 are photographs showing states 7 days after colony formation of the *Trichophyton* in each test sample.

TABLE 6

| Sample name | Concentration (mg/ml) | Determination |
|---|---|---|
| LYZOX | 10 | − |
|  | 5 | ++ |
|  | 2.5 | ++ |
|  | 1 | +++ |
| Decanoic acid | 1.5 | − |
|  | 1 | ++ |
|  | 0.9 | +++ |
|  | 0.8 | +++ |
| LYZOX/ | 0.3/0.6 | − |
| Decanoic acid | 0.2/0.4 | − |
|  | 0.1/0.2 | − |
|  | 0.05/0.1 | ++ |
| Lysozyme | 5 | ++ |
|  | 2.5 | +++ |
| Chitosan | 5 | ++ |
|  | 2.5 | +++ |
| Lysozyme/ | 5/5 | ++ |
| Chitosan | 2.5/2.5 | ++ |
| Lysozyme/ | 0.25/0.25/1 | − |
| Chitosan/ | 0.2/0.2/0.8 | ++ |
| Decanoic acid | 0.05/0.05/0.2 | ++ |
|  | 0.025/0.025/0.1 | ++ |

| Mycelial growth rate taking control as 100 | Determination |
|---|---|
| 0% | − |
| 1 to 20% | + |
| 21 to 90% | ++ |
| 91 to 100% | +++ |

The MIC (minimum inhibitory concentration) of the LYZOX and the decanoic acid were as follows.

| LYZOX (used alone) | 10 mg/ml |
|---|---|
| Decanoic acid (used alone) | 1.5 mg/ml |

When LYZOX and decanoic acid were used in combination, the MIC (minimum inhibitory concentration) of the LYZOX and the decanoic acid were as follows.

| LYZOX (used in combination) | 0.1 mg/ml |
|---|---|
| Decanoic acid (used in combination) | 0.2 mg/ml |

Namely, when LYZOX and decanoic acid were used in combination, the FIC index with respect to growth suppression of the *Trichophyton* was 0.143, and it was therefore determined that a synergistic effect existed.

INDUSTRIAL APPLICABILITY

According to the present invention, it is possible to provide a novel composition having an antifungal activity without having to rely on existing compositions having an antifungal activity including activity against *Candida* or on combinations of such compositions.

What is claimed is:

1. A method for suppressing a fungus by applying (i) a complex formed by bonding lysozyme to chitosan, and (ii) decanoic acid, wherein the suppression of the fungus is caused by an antifungal activity of a *Trichophyton* proliferation suppression action.

* * * * *